United States Patent [19]

Sprecker et al.

[11] Patent Number: 4,639,330

[45] Date of Patent: Jan. 27, 1987

[54] ALKYL-SUBSTITUTED SPIRODECENONE DERIVATIVES, ORGANOLEPTIC UTILITY THEREOF AND PROCESSES FOR PREPARING SAME

[75] Inventors: Mark A. Sprecker, Sea Bright; Marie R. Hanna, Hazlet, both of N.J.

[73] Assignee: International Flavors & Fragrances Inc., New York, N.Y.

[21] Appl. No.: 842,207

[22] Filed: Mar. 21, 1986

[51] Int. Cl.$^4$ .............................................. A61K 7/46
[52] U.S. Cl. .................... 252/522 R; 568/349; 568/367; 424/70; 424/71; 252/174.11
[58] Field of Search ...................... 252/522 R, 174.11; 568/349, 367; 424/70, 71

[56] References Cited

U.S. PATENT DOCUMENTS 4,052,457 10/1977 Nagakura et al. .................. 568/367
4,261,866 4/1981 Barton et al. ........................ 568/367

OTHER PUBLICATIONS

Nerdel et al., Ann. Chem, vol. 710, pp. 90-97 (1967).
Tanaka et al., J. Chem Soc, Chem Comm., pp. 188-189 (1967).
Soboleva et al., Chem. Abst., vol. 80, #145536r (1975).

Primary Examiner—James H. Reamer
Attorney, Agent, or Firm—Arthur L. Liberman

[57] ABSTRACT

Described are alkyl-substituted spirodecenone derivatives defined according to the structure:

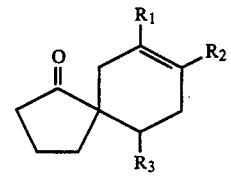

wherein one of $R_1$ or $R_2$ is hydrogen and the other of $R_1$ or $R_2$ is methyl; and wherein $R_3$ represents $C_3$–$C_4$ alkyl, and uses thereof in augmenting or enhancing the aroma of perfume compositions, colognes and perfumed articles including, but not limited to, solid or liquid anionic, cationic, nonionic or zwitterionic detergents, fabric softener compositions, fabric softener articles and hair preparations; as well as processes for preparing said alkyl-substituted spirodecenone derivatives.

15 Claims, 7 Drawing Figures

GLC PROFILE FOR FRACTION 2 OF EXAMPLE II. 2ND DISTILLATION

GLC PROFILE FOR EXAMPLE I.

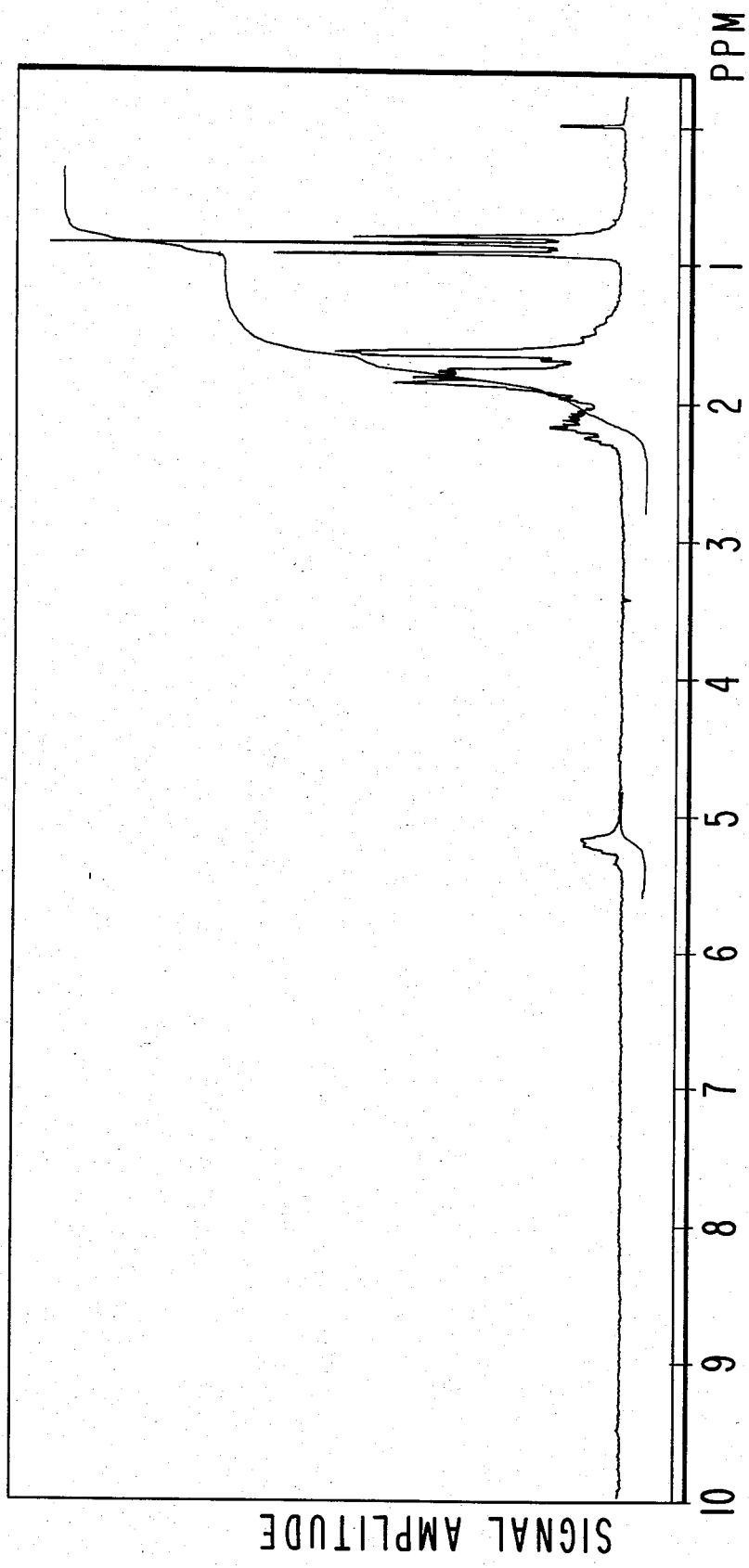

NMR SPECTRUM FOR FRACTION 9 OF EXAMPLE II.

ALKYL-SUBSTITUTED SPIRODECENONE DERIVATIVES, ORGANOLEPTIC UTILITY THEREOF AND PROCESSES FOR PREPARING SAME

BACKGROUND OF THE INVENTION

The instant invention relates to alkyl-substituted spirodecenone derivatives defined according to the structure:

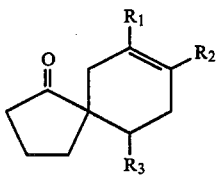

wherein one of $R_1$ or $R_2$ is hydrogen and the other of $R_1$ or $R_2$ is methyl and $R_3$ represents $C_3$–$C_4$ alkyl, and uses of same in augmenting or enhancing the aroma of perfume compositions, perfumed articles and colognes.

Inexpensive chemical compounds which can provide spicy, floral, rose-like, minty, jasmine and woody aromas with sweet, cardamon, natural balsam, floral, spicy, camphoraceous, vetiver-like, woody, fig-like, and date-like undertones are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enchance or augment the fragrance notes provided by natural essential oils or compositions thereof. Unfortunately, many of the synthetic materials either have the desired nuances only to a relatively small degree or they contribute undesirable or unwanted odor to the compositions.

Spiro ketones including spirodecenones as well as spiroundecenones are well known in the prior art and their utilities are known in perfumery.

Thus, Japanese Published Application No. 76/65738 (abstracted at Chemical Abstracts 85:123440f) (corresponding to U.S. Pat. No. 4,052,457 issued on Oct. 4, 1977) discloses the compound having the structure:

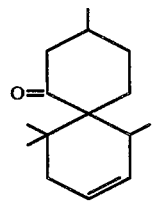

as being useful in perfumery and further discloses the process according to the reaction:

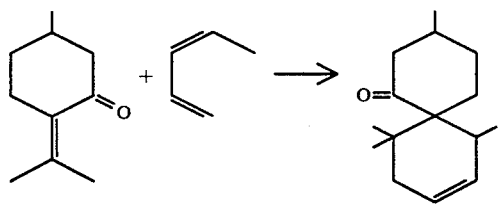

Nerdel and Dahl, *Ann. Chim.*, 710, 90 (1967) discloses the compound having the structure:

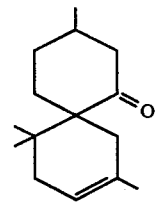

and the generic process, to wit:

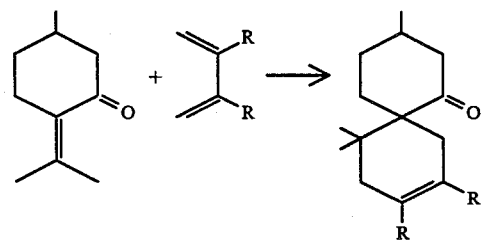

(wherein R represents hydrogen or methyl).

Tanaka, et al, Chem. Comm. 1967, page 188 (title of paper: "The Total Synthesis of Chamigrene" discloses the compound having the structure:

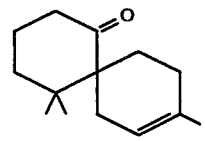

U.S. Pat. No. 4,261,866 issued on Apr. 14, 1981 (Class 252, Subclass 522 R) discloses the genus of compounds having the structure:

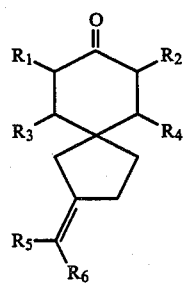

wherein $R_1$–$R_6$ each represents hydrogen or lower alkyl. U.S. Pat. No. 4,261,866 discloses the broad genus, to wit:

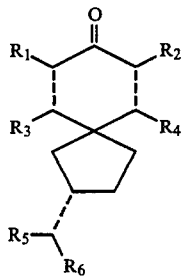

wherein each of the dashed lines represent carbon-carbon single bonds and carbon-carbon double bonds. The compounds disclosed in U.S. Pat. No. 4,261,866 are indicated to be useful in perfumery.

However, the alkyl-substituted spirodecenone derivatives of our invention have unexpected, unobvious and advantageous perfumery properties when compared with the perfumery properties of the prior art.

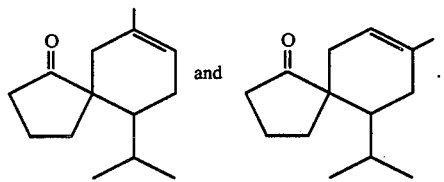

FIG. 2 is the NMR spectrum for the mixture of compounds produced according to Example I having the structures:

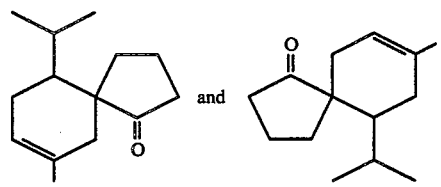

(Conditions: Field strength: 100 MHz; Solvent: CFCl$_3$).

Figure 3:
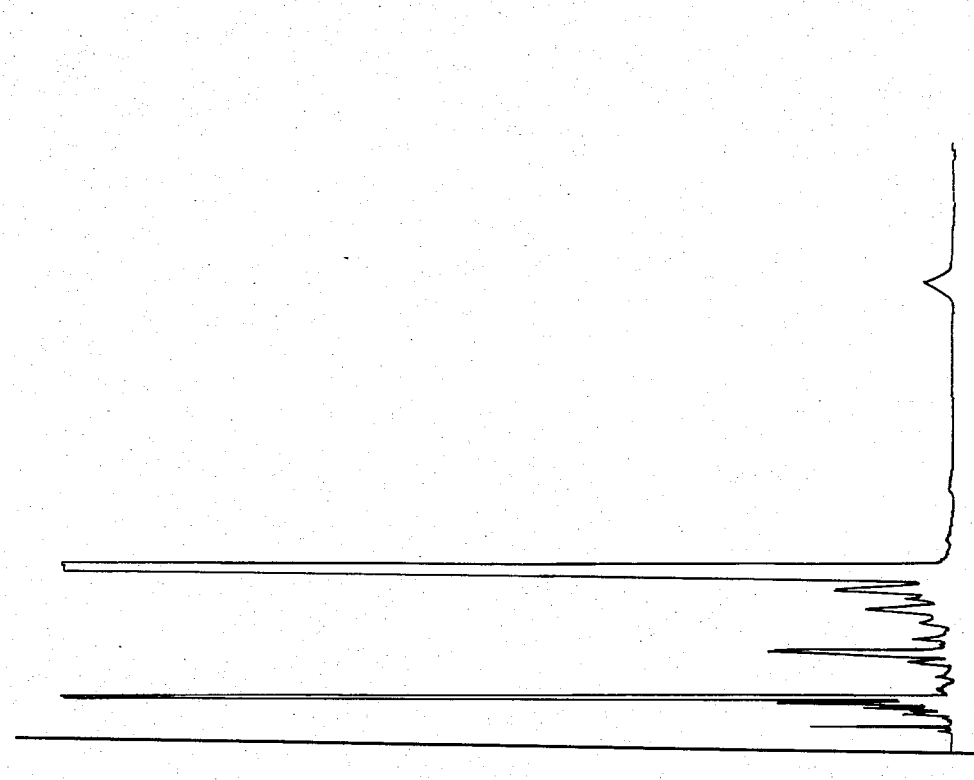

FIG. 3 is the GLC profile for Fraction 2 of the second distillation of the reaction product of Example II containing the compounds having the structures:

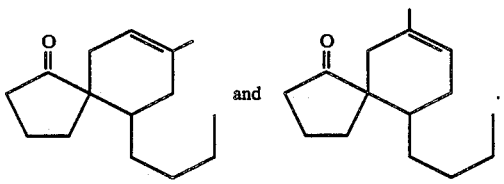

Figure 4:
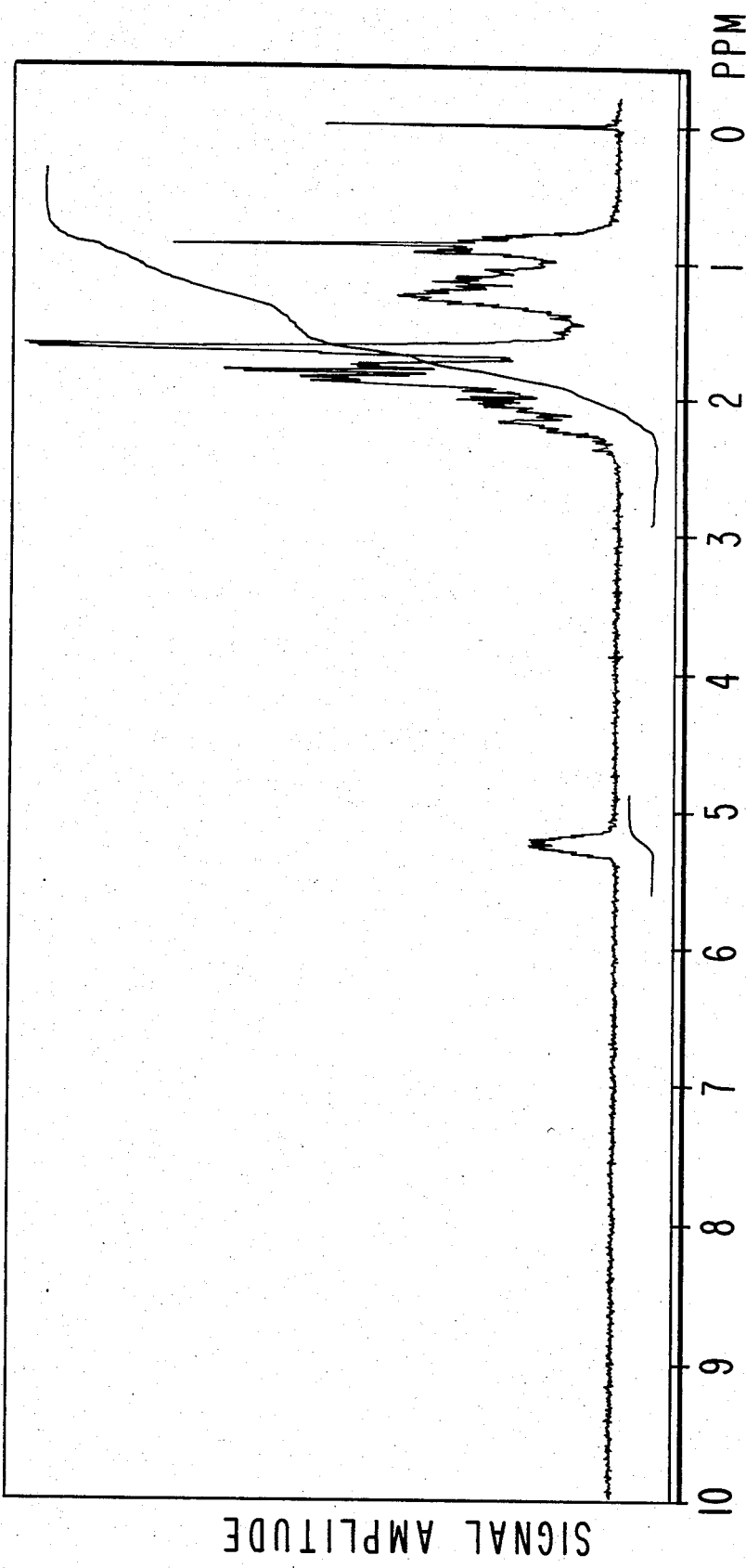

FIG. 4 is the NMR spectrum for Fraction 9 of the second distillation of the reaction product of Example II containing the compounds having the structures:

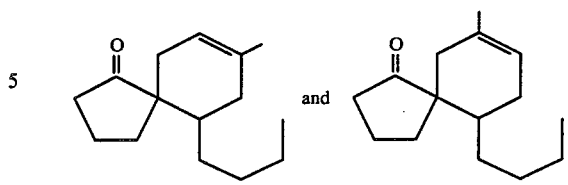

(Conditions: Field strength: 100 MHz; Solvent: CFCl$_3$).

Figure 5:
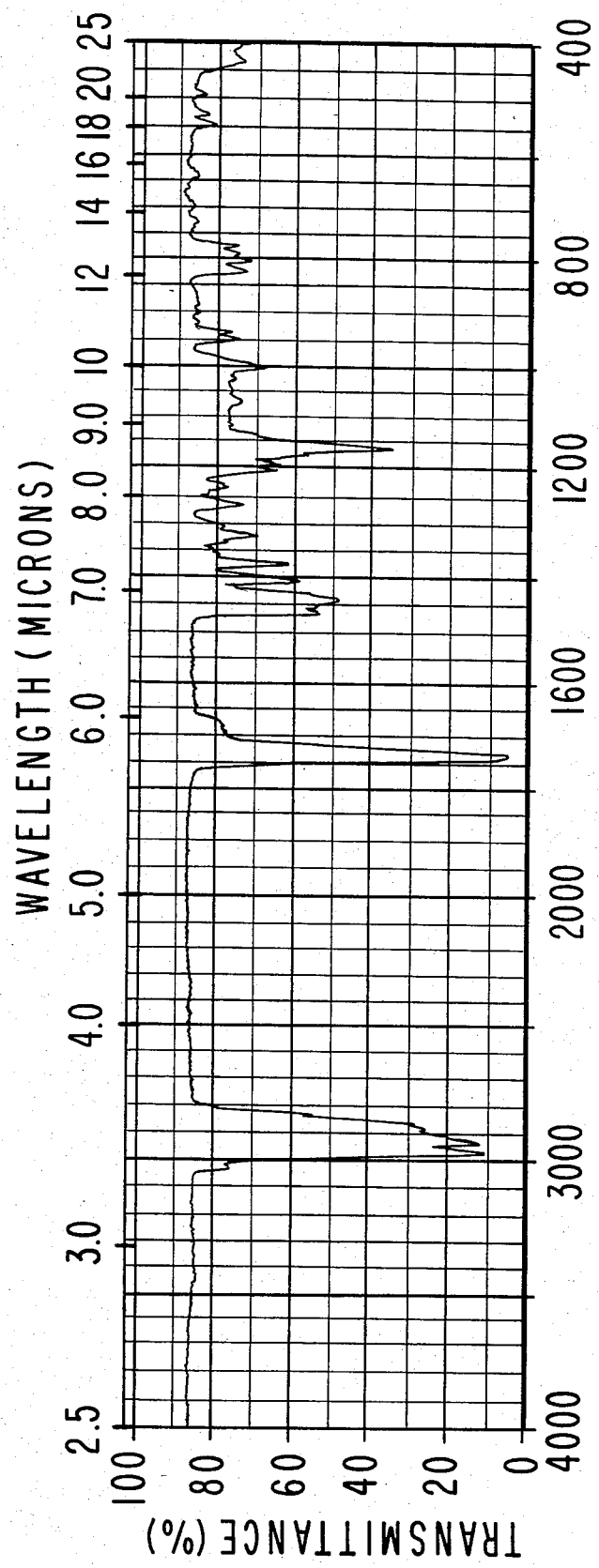

FIG. 5 is the infra-red spectrum for Fraction 9 of the second distillation of the reaction product of Example II containing the compounds having the structures:

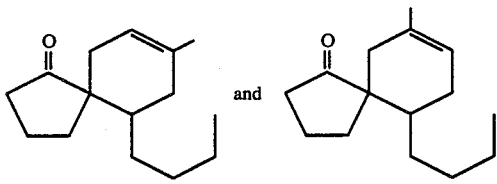

Figures 6, 7:
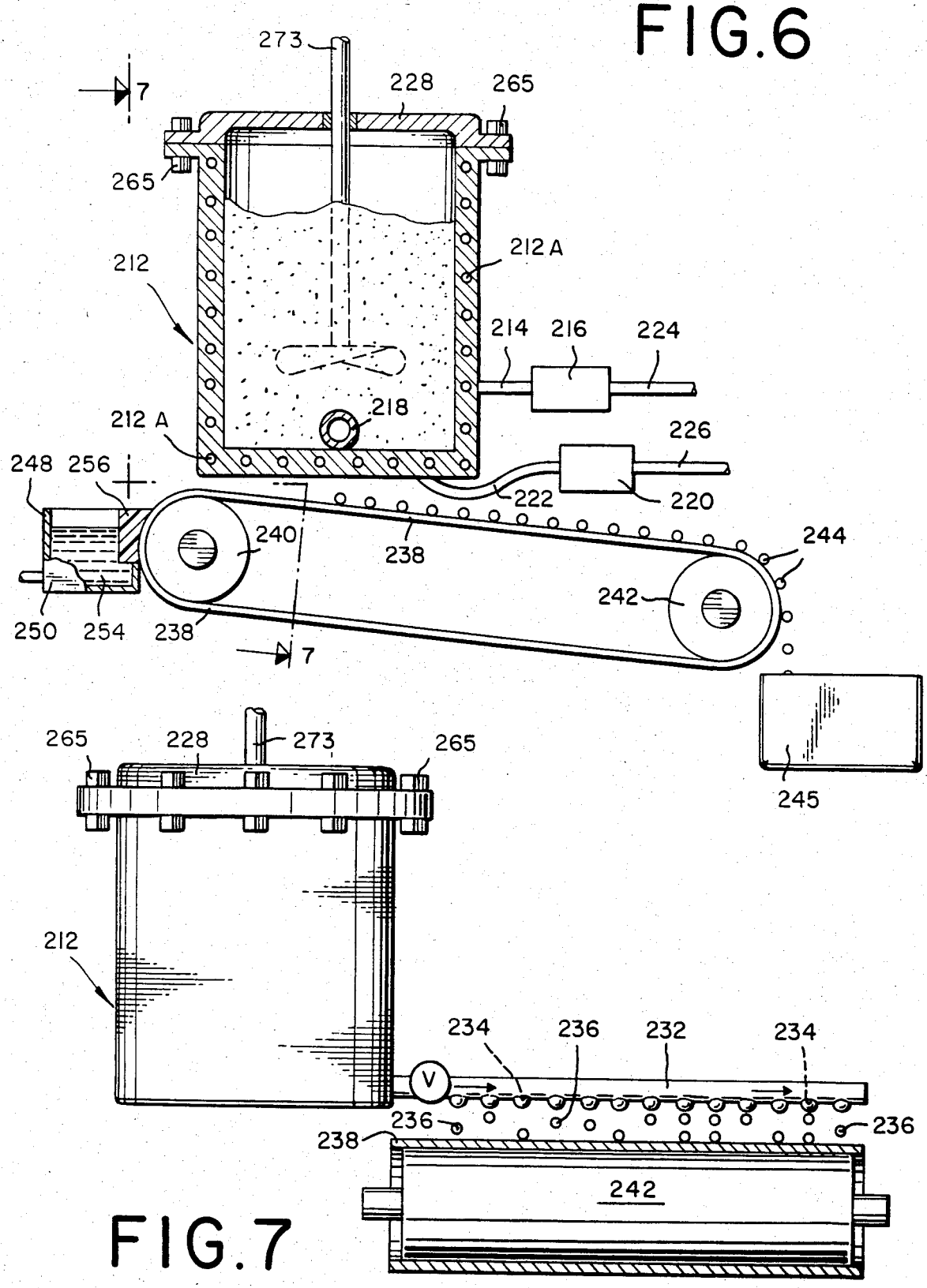

FIG. 6 is a partial side elevation view and partial sectional view of an apparatus for forming polymer pellets containing at least one of the alkyl-substituted spirodecenone derivatives of our invention.

FIG. 7 is a section taken along the line 7—7 of FIG. 6.

DETAILED DESCRIPTION OF THE DRAWINGS

Referring to FIGS. 6 and 7, the apparatus used in producing polymeric fragrances containing the alkyl-substituted spirodecenone derivatives of our invention comprises a device for forming scented polyolefin (for example) pellets, which comprises a vat or container 212 into which a mixture of polyolefin such as polyethylene and an aromatic substance or scented material is placed (in this case at least one of the alkyl-substituted spirodecenone derivatives of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the alkyl-substituted spirodecenone derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the alkyl-substituted spirodecenone derivatives of our invention) are added to the polyolefin.

After the scent imparting material (e.g., a composition containing at least one of the alkyl-substituted spirodecenone derivatives of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., at least one of the alkyl-substituted spirodecenone derivatives of our invention) will continuously drop through orifices 234 downwardly from conduit 232. During this time the temperature of the polymer (e.g., polyolefin) and scent imparting material (e.g., a mixture containing at least one of the alkyl-substituted spirodecenone derivatives of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the alkyl-substituted spirodecenone derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides alkyl-substituted spirodecenone derivatives defined according to the generic structure:

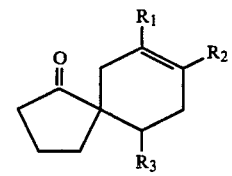

wherein one of $R_1$ or $R_2$ is hydrogen and the other of $R_1$ or $R_2$ is methyl; and wherein $R_3$ is $C_3$–$C_4$ alkyl.

The compositions of matter of our invention produced according to the processes of our invention are capable of augmenting, enhancing or providing spicy, floral, rose-like, minty, jasmine and woody aromas with sweet, cardamon, natural balsam, floral, spicy, camphoraceous, vetiver-like, woody, fig-like and date-like undertones to perfume compositions, colognes and perfumed articles (e.g., solid or liquid anionic, cationic, nonionic or zwitterionic detergents, fabric softener articles, drier-added fabric softener articles, fabric softener compositions, cosmetic powders, hair preparations, perfumed polymers and the like).

The substances of our invention are prepared by means of reacting an alkylidene cyclopentanone having the structure:

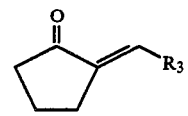

with isoprene having the structure:

in order to form one or more of the alkyl-substituted spirodecenone derivatives of our invention according to the reaction:

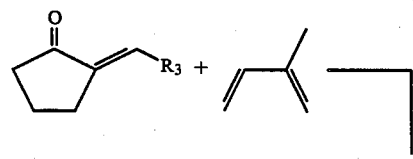

-continued

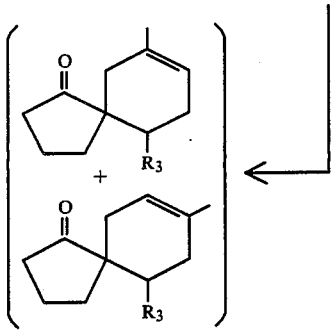

wherein R₃ represents C₃–C₄ alkyl. The reaction takes place in the presence of a Lewis acid catalyst such as aluminum chloride, zinc chloride or stannic chloride, ethyl dialuminum chloride, or diethyl aluminum chloride and in the presence of a solvent inert to the reactants or reaction product such as methylene dichloride, 1,1-dichloroethane or toluene.

The reaction temperature may vary from about 5° C. up to about 50° C. and the reaction time may vary from about one hour up to about fifteen hours.

The mole ratio of alkylidiene cyclopentanone having the structure:

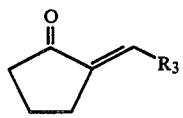

to isoprene having the structure:

may vary from about 0.5:1.5 up to about 1.5:0.5 with a mole ratio of about 1:1 being desirable.

At the end of the reaction time, the reaction mass is usually washed with such materials as saturated aqueous sodium chloride followed by aqueous sodium carbonate (e.g., a 10% aqueous solution of sodium carbonate).

The thus-washed material is fractionally distilled and the resulting fractions are selected according to GLC, NMR and IR analysis as well as odor acceptability.

Examples of the alkyl-substituted spirodecenone derivatives are set forth in the following Table I:

TABLE I

| Alkyl-Substituted Spiro-decenone Derivative of Our Invention | Perfumery Properties |
| --- | --- |
| Mixture of compounds having the structures: 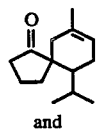 and | A spicy, rose-like, minty aroma with cardamon, fig-like, date-like, vetiver-like, floral and woody undertones. |

TABLE I-continued

| Alkyl-Substituted Spiro-decenone Derivative of Our Invention | Perfumery Properties |
| --- | --- |
| produced according to Example I, bulked distillation fractions 7–12. | |
| Mixture of compound having the structures: and produced according to Example II, bulked fractions 7–13. | A floral, jasmine, minty and woody aroma with sweet, natural balsam, lemon, spicy, woody and camphoraceous undertones. |

One or more of the alkyl-substituted spirodecenone derivatives prepared in accordance with the processes of our invention and one or more auxiliary perfume ingredients including, for example, alcohols, aldehydes, ketones other than the alkyl-substituted spirodecenone derivatives of our invention, terpenic hydrocarbons, nitriles, esters, lactones, natural essential oils and synthetic essential oils may be admixed so that the combined odors of the individual components produce a pleasant and desired fragrance, particularly and preferably in the woody, minty, herbaceous, spicy and tagette fragrances. Such compositions usually contain:

(a) the main note or the "bouquet" or foundation stone of the composition;

(b) modifiers which round-off and accompany the main note;

(c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the alkyl-substituted spirodecenone derivatives prepared in accordance with the processes of our invention can be used to alter, modify or enhance the aroma characteristics of a perfume composition, for example, by utilizing or moderating the olfactory reaction contributed by another ingredient in the composition.

The amount of the alkyl-substituted spirodecenone derivatives prepared in accordance with the processes of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the alkyl-substituted spirodecenone derivatives prepared in accordance with the processes of our invention or even less (e.g., 0.005%) can be used to impart, augment or enhance spicy, floral, rose-like, minty, jasmine and woody aromas with sweet, cardamon, natural-balsam, floral, spicy, camphoraceous, vetiver-like, woody, fig-like and date-like undertones to soaps, cosmetics, anionic, cationic, nonionic or zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The alkyl-substituted spirodecenone derivatives prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of the alkyl-substituted spirodecenone derivatives prepared in accordance with the processes of our invention will suffice to impart, augment or enhance spicy, floral, rose-like, minty, jasmine and woody aromas with sweet, cardamon, natural-balsam, floral, spicy, camphoraceous, vetiver-like, woody, fig-like and date-like undertones. Generally, no more than 6% of the alkyl-substituted spirodecenone derivatives of our invention based on the ultimate end product is required in the perfumed article. Accordingly, the range of use of the alkyl-substituted spirodecenone derivatives of our invention in perfumed articles, per se, is from about 0.005% up to about 6% by weight based on the perfumed article.

In addition, the perfume composition or fragrance composition of our invention can contain a vehicle or carrier for the alkyl-substituted spirodecenone derivatives prepared in accordance with the processes of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combination thereof) or components for encapsulating the composition (such as by coacervation) or using prepolymers such as urea-formaldehyde prepolymers which are able to form a urea-formaldehyde polymer capsule around a liquid perfume center.

It will thus be apparent that the alkyl-substituted spirodecenone derivatives prepared in accordance with the processes of our invention can be utilized to alter, modify or enhance sensory properties particularly organoleptic properties such as fragrances of a wide variety of consumable materials.

The following Examples I and II set forth means for preparing the alkyl-substituted spirodecenone derivatives of our invention. The examples including and following Example III, infra set forth illustrations of organoleptic utilities of the alkyl-substituted spirodecenone derivatives of our invention.

All parts and percentages given herein are by weight unless otherwise specified.

EXAMPLE I

PREPARATION OF ETHYL ISOPROPYL SPIROCYCLOHEXENYL CYCLOPENTANONE

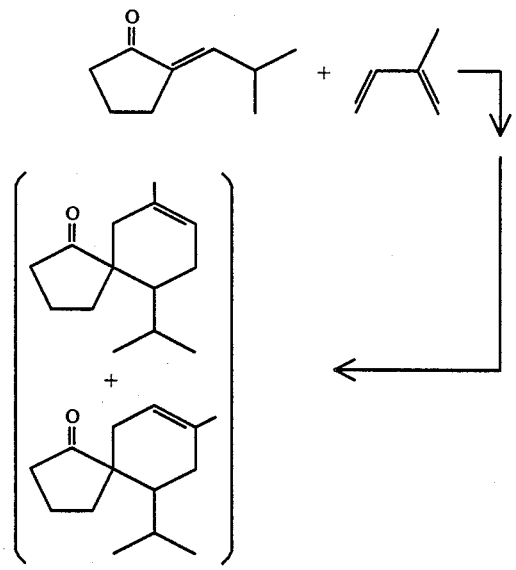

Into a 2 liter reaction vessel equipped with stirrer, thermometer, cooling bath and addition funnel are placed 500 ml methylene dichloride and 7 grams of aluminum trichloride. With stirring over a period of 15 minutes, 610 grams (5 moles) of isobutylidene cyclopentanone having the structure:

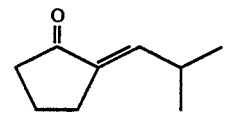

is added to the reaction mass while maintaining the reaction at a temperature of 20° C.

Over a three hour period while maintaining the reaction mass at a temperature in the range of 20°-25° C., 476 grams (7 moles) of isoprene is added with stirring.

The reaction mass is then heated to 40° C. and maintained at 40° C. with stirring for a period of four hours.

At the end of the four hour period, the reaction mass is admixed with 1 liter of saturated sodium chloride solution and the organic phase is separated. The organic phase is then washed with 10% aqueous sodium carbonate (1 liter) and distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | /30 | /100 | 5 min/ |
| 2 | 77 | 130 | 2.5 |
| 3 | 90 | 180 | 2.5 |

Fractions 2 and 3 are bulked and redistilled on 12"×1½" Goodloe column yielding the following fractions:

| Fraction No. | Vapor Temp. (°C.) | Liquid Temp. (°C.) | Vacuum mm/Hg. Pressure |
|---|---|---|---|
| 1 | 65/ | 120/ | 3 mm |
| 2 | 65 | 120 | 3 mm |
| 3 | 106 | 125 | 3 mm |
| 4 | 109 | 177 | 3 mm |
| 5 | 108 | 123 | 2.5 |
| 6 | 110 | 126 | 2.5 |
| 7 | 110 | 125 | 2.5 |
| 8 | 110 | 125 | 2.5 |
| 9 | 110 | 125 | 2.5 |
| 10 | 110 | 125 | 2.5 |
| 11 | 109 | 125 | 2.5 |
| 12 | 109 | 125 | 2.5 |
| 13 | 110 | 130 | 2.5 |
| 14 | 110 | 130 | 2.5 |
| 15 | 110 | 130 | 2.5 |

Bulked fractions 7–12 of the foregoing distillation has a spice, rose-like and minty aroma with cardamon, fig-like, date-like, vetiver-like, floral and woody undertones.

Figure 1:
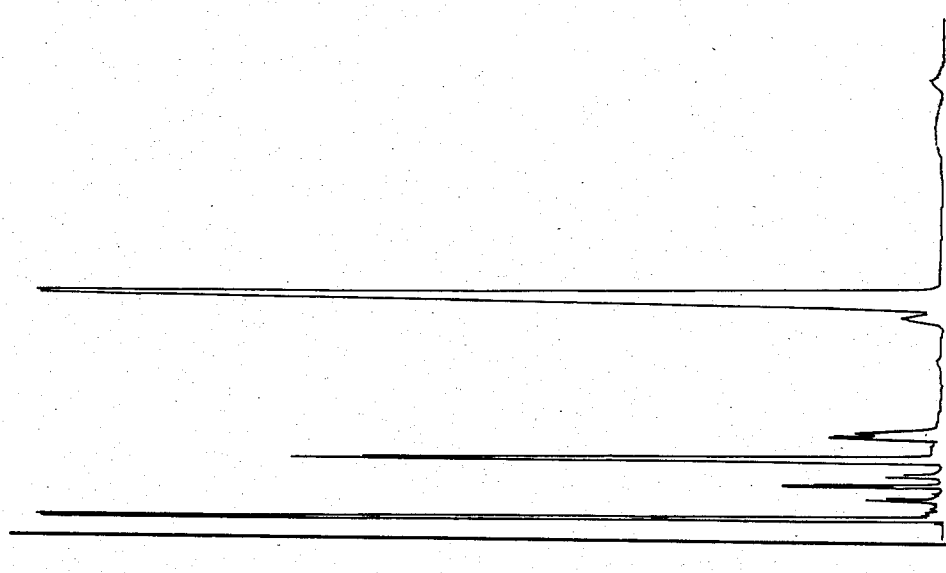
FIG. 1 is the GLC profile for the crude reaction product of Example I containing the compounds having the structures.

FIG. 1 is the GLC profile of the crude reaction product.

FIG. 2 is the NMR spectrum for the mixture of compounds having the structures:

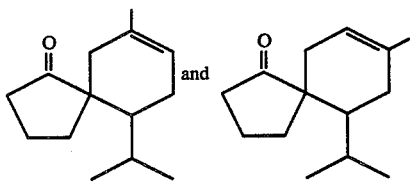

prepared according to the foregoing procedure.

EXAMPLE II

PREPARATION OF METHYL-n-BUTYL SPIROCYCLOHEXENYL CYCLOPENTANONE

Reaction:

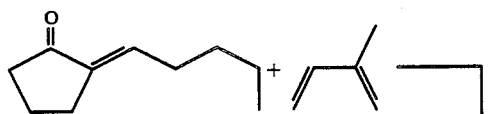

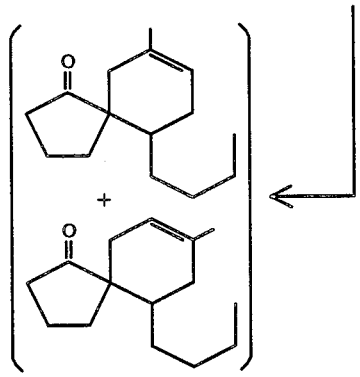

Into a 1 liter reaction vessel equipped with stirrer, thermometer, cooling bath and reflux condenser and addition funnel is placed 200 ml methylenedichloride and 14 grams of aluminumtrichloride. While maintaining the reaction mass at 10° C., over a period 15 minutes, 213 grams (1.4 moles) of pentylidene cyclopentanone having the structure:

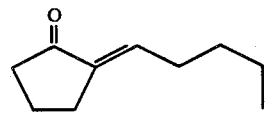

is added to the reaction mass.

Over a period of one hour while maintaining the reaction mass at 10° C., 136 grams (2 moles) of isoprene is added to the reaction mass with stirring. The reaction mass is then stirred for a period of four hours. At the end of the four hour period, the reaction mass is distilled on a 2" splash column yielding the following fractions:

| Fraction No. | Vapor Temp. (°C.) | Liquid Temp. (°C.) | Vacuum mm/hg. Pressure |
|---|---|---|---|
| 1 | / | / | 100 mm |
| 2 | 130 | 140 | 5 mm |
| 3 | 130/140 | 170/200 | 3 nn |

Fractions 2 and 3 are bulked and redistilled on a 12"×1" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 87/110 | 131/135 | 2.2/2.0 | 2:1 |
| 2 | 113 | 133 | 1.6 | 2:1 |
| 3 | 113 | 135 | 1.6 | 2:1 |
| 4 | 113 | 134 | 1.6 | 2:1 |
| 5 | | | | 2:1 |
| 6 | 116 | 136 | 1.6 | 100% |
| 7 | 118 | 134 | 1.6 | 100% |
| 8 | 118 | 134 | 1.6 | 100% |
| 9 | 117 | 134 | 1.6 | 100% |
| 10 | 117 | 135 | 1.6 | 100% |
| 11 | 112 | 137 | 1.6 | 100% |
| 12 | 110 | 140 | 0.8 | 100% |
| 13 | 110 | 140 | 0.8 | 100% |
| 14 | 100 | 180 | 0.6 | 100% |

Bulked fractions 7–13 of the foregoing distillation has a floral, jasmine, minty and woody aroma with sweet, natural balsam, lemon, spicy, woody and camphoraceous undertones.

FIG. 3 is the GLC profile for fractions 2 of the second distillation containing the compounds having the structures:

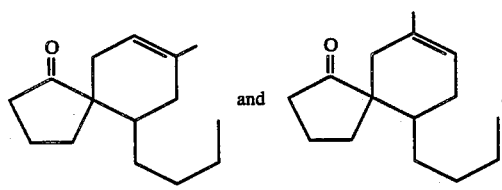

FIG. 4 is the NMR spectrum for fraction 9 of the foregoing distillation containing the compounds having the structures:

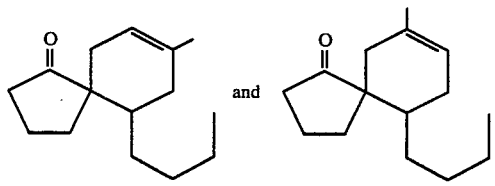

(Conditions: Field strength: 100 MHg; Solvent: CFCl₃).

FIG. 5 is the infra-red spectrum for fraction 9 of the foregoing distillation containing the compounds having the structures:

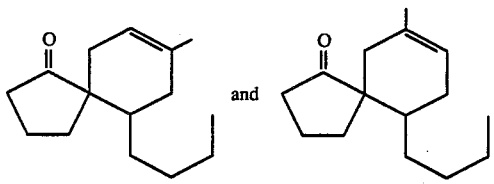

EXAMPLE III

PERFUME FORMULATIONS

The following woody cologne perfume formulations are prepared:

| Ingredients | Parts by Weight | | |
|---|---|---|---|
| | III(A) | III(B) | III(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-methyl-4-hydroxy amyl Δ³cyclohexene carboxaldehyde (LYRAL ® Trademark of International Flavors & Fragrances Inc. of New York, New York) | 40 | 40 | 40 |
| Ylang oil | 2 | 2 | 2 |
| Petitgrain Paraguay | 10 | 10 | 10 |
| γ-Methyl ionone | 20 | 20 | 20 |
| Vetiver Venezuela | 18 | 18 | 18 |
| 3-α-Methyl-dodecahydro-6,6,9a-trimethylnaptho[2,1-b]furan | 5 | 5 | 5 |
| Product produced by the reaction of acetic anhydride, polyphosphoric acid and 1,5,9-trimethyl cyclo-dodecatriene-1,5,9 according to the process of Example I of U.S. Letters Pat. No. 3,718,697, the specification for which is incorporated by reference herein | 50 | 50 | 50 |
| Octahydro-9,9-dimethyl-1,6-methanonaphthalene-1-[2H]—ol produced according to Example III of U.S. Letters Pat. No. 3,996,169, the specification for which is incorporated by refence herein | 50 | 50 | 50 |
| Mixture of compounds having the structures: | 12 | 0 | 0 |

and

| Ingredients | Parts by Weight | | |
|---|---|---|---|
| | III(A) | III(B) | III(C) | prepared according to Example I, bulked fractions 7–12 of second distillation

| Mixture of compounds having the structures: | 0 | 12 | 0 | and prepared according to Example II, bulked fractions 7–13 of second distillation.

| A 50:50 mixture of the composition of matter containing the compounds having the structures: | 0 | 0 | 12 | and prepared according to Example I (bulked fractions 7–12) and a mixture of the compounds having the structures:

and

-continued

| Ingredients | Parts by Weight | | |
|---|---|---|---|
| | III(A) | III(B) | III(C) |

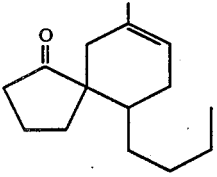

(bulked fractions 7-13) prepared according to Example II.

The 50:50 (weight:weight) mixture of compounds having the structures:

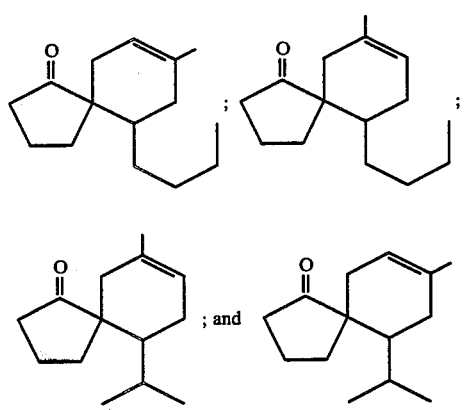

(mixture of products of Example I, bulked distillation fractions 7-12 in Example II, bulked distillation fractions 7-13) imparts to the "woody cologne" composition of Example III(C), a spicy, floral, rose-like, minty, jasmine and woody aroma with sweet, cardamon, natural balsam, floral, spicy, camphoraceous, vetiver, woody, fig-like and date-like undertones. Accordingly, the composition of Example III(C) can be described as a "woody cologne" composition with spicy, floral, rose-like, minty, jasmine and woody topnotes and sweet, cardamon, natural balsam, floral, spicy, camphoraceous, vetiver, woody, fig-like and date-like undertones.

EXAMPLE IV

PREPARATION OF COSMETIC POWDER COMPOSITION

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Mixture of compounds having the structures: 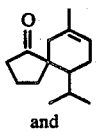 and | A spice, rose-like, and minty aroma with cardamon-like, fig-like, date-like, vetiver, floral and woody undertones. |
|  produced according to Example I (bulked fractions 7-12). | |
| Mixture of compounds having the structures:  and  prepared according to Example II, bulked fractions 7-13. | A floral, jasmine, minty and woody aroma with sweet, natural balsam, lemon, spicy, woody and camphoraceous undertones. |
| Perfume composition of Example III(A). | A spicy, rose-like and minty topnotes and cardamon fig-like, date-like, vetiver, floral and woody undertones. |
| Perfume composition of Example III(B). | Floral, jasmine, minty and woody topnotes and sweet, natural balsam, lemon, spicy, woody and camphoraceous undertones. |
| Perfume composition of Example III(C). | Spicy, floral, rose-like, minty, jasmine and woody topnotes and sweet, cardamon, natural balsam, floral, spicy, camphoraceous, vetiver, woody, fig-like and date-like undertones. |

EXAMPLE V

PERFUMED LIQUID DETERGENTS

Concentrated liquid detergents (Lysine salt of n-dodecylbenzene sulfonic acid as more specifically described in U.S. Pat. No. 3,948,818 issued on Apr. 6, 1976 incorporated by reference herein) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. the detergents all possess excellent aromas as set forth in Table II of Example IV, the intensity increasing with greater concentrations of substances as set forth in Table II of Example IV.

EXAMPLE VI

PREPARATION OF COLOGNES AND HANDKERCHIEF PERFUMES

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII
PREPARATION OF SOAP COMPOSITIONS

One hundred grams of soap chips [per sample] (IVORY ®, produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling manifest aromas as set forth in Table II of Example IV.

EXAMPLE VIII
PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
| --- | --- |
| "NEODOL" ® 45-11 (a $C_{12}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
57% $C_{20\text{-}22}$HAPS;
22% isopropyl alcohol;
20% antistatic agent; and
1% of one of the substances as set forth in Table II of Example IV.

Fabric softening compositions prepared according to Example I at column 15 of U.S. Pat. No. 3,632,396 having the aroma characteristics as set forth in Table II of Example IV, supra, consist of a substrate coating having a weight of about 3 grams per 100 square inches of substrate a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example IV, supra.

EXAMPLE X
HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% of food grade ethanol. 8.0 Grams of the polymer is dissolved in the alcohol. The following ingredients are added to the PVP/VA alcoholic solution:

| Ingredient | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example IV, supra | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI
CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio; 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

What is claimed is:

1. An alkyl-substituted spirodecenone derivative defined according to the structure:

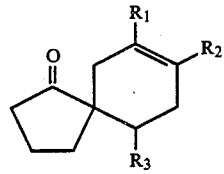

wherein one of $R_1$ or $R_2$ is methyl and the other of $R_1$ or $R_2$ is hydrogen; and wherein $R_3$ represents $C_3$–$C_4$ alkyl.

2. A process for augmenting or enhancing the aroma of a consumable material selected from the group consisting of perfume compositions, colognes and perfumed articles comprising the step of adding to said consumable material, an aroma augmenting or enhancing quantity of the product of claim 1.

3. The product of claim 1 having the structure:

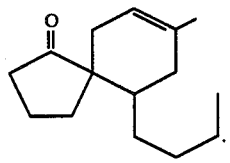

4. The product of claim 1 having the structure:

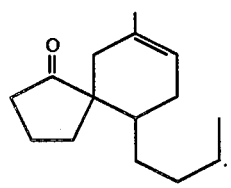

5. The product of claim 1 having the structure:

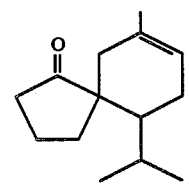

6. The product of claim 1 having the structure:

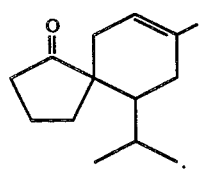

7. A mixture of alkyl-substituted spirodecenone derivatives having the structures:

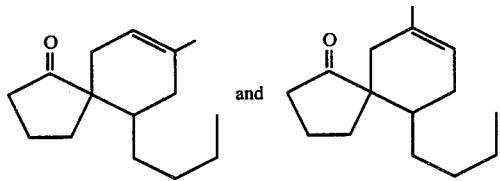

8. A mixture of alkyl-substituted spirodecenone derivatives having the structures:

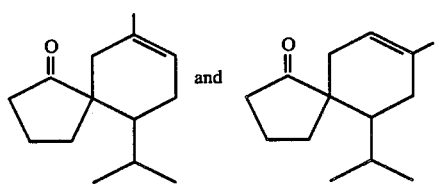

9. A process for augmenting or enhancing the aroma of a consumable material selected from the group consisting of perfume compositions, colognes and perfumed articles comprising the step of adding to said consumable material, an aroma augmenting or enhancing quantity of the product of claim 7.

10. A process for augmenting or enhancing the aroma of a consumable material selected from the group consisting of perfume compositions, colognes and perfumed articles comprising the step of adding to said consumable material, an aroma augmenting or enhancing quantity of the product of claim 8.

11. A product containing a mixture of compounds defined according to the structure:

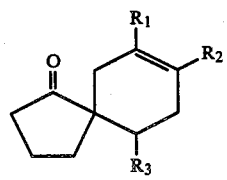

wherein one of $R_1$ or $R_2$ is hydrogen and the other of $R_1$ or $R_2$ is methyl and $R_3$ is the same $C_3$–$C_4$ alkyl produced according to the process consisting essentially of the steps of:

(i) reacting an alkylidenecyclopentanone having the structure:

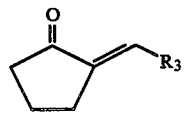

with isoprene having the structure:

in the presence of a Lewis acid catalyst and an inert solvent for a period of time sufficient to cause the production of a significant quantity of the compounds having the structure:

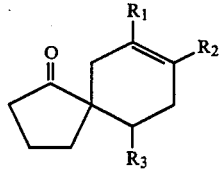

the reaction temperature varying from about 5° C. up to about 50° C. and the reaction time varying from about 1 hour up to about 15 hours with the mole ratio of alkylidenecyclopentanone to isoprene varying from about 0.5:1.5 up to about 1.5:0.5 and then (ii) recovering the compounds having the structure:

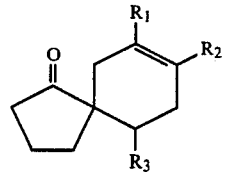

from the resulting reaction product by fractional distillation.

12. The product of claim 11 wherein $R_3$ is isopropyl with said fractional distillation being carried out at a vapor temperature of from 109°–110° C. and a vacuum of 2.5 mm/Hg pressure.

13. The product of claim 11 wherein $R_3$ is n-butyl with said fractional distillation being carried out at a vapor temperature of from 110°–118° C. and a vacuum of from 0.8–1.6 mm/Hg pressure.

14. A process for augmenting or enhancing the aroma of a consumable material selected from the group consisting of perfume compositions, colognes and perfumed articles comprising the step of adding to said consumable material an aroma augmenting or enhancing quantity of the product of claim 12.

15. A process for augmenting or enhancing the aroma of a consumable material selected from the group consisting of perfume compositions, colognes and perfumed articles comprising the step of adding to said consumable material an aroma augmenting or enhancing quantity of the product of claim 13.

* * * * *